(12) United States Patent
Viovy et al.

(10) Patent No.: US 10,130,949 B2
(45) Date of Patent: Nov. 20, 2018

(54) MICROFLUIDIC SYSTEM

(75) Inventors: Jean-Louis Viovy, Paris (FR); Laurent Malaquin, Linas (FR); Stefano Begolo, Pasadena, CA (US); Anaïs Ali Cherif, Paris (FR); Stephanie Descroix, Paris (FR)

(73) Assignees: SORBONNE UNIVERSITE, CENTRE NATIONAL DE LA RECHERCHE SCIENTIFIQUE, Paris (FR); ETAT FRANCAIS REPRESENTED BY MINISTERE DE LA DEFENSE, Paris (FR)

( * ) Notice: Subject to any disclaimer, the term of this patent is extended or adjusted under 35 U.S.C. 154(b) by 252 days.

(21) Appl. No.: 14/345,910

(22) PCT Filed: Jul. 24, 2012

(86) PCT No.: PCT/IB2012/053766
§ 371 (c)(1),
(2), (4) Date: Jun. 30, 2014

(87) PCT Pub. No.: WO2013/041983
PCT Pub. Date: Mar. 28, 2013

(65) Prior Publication Data
US 2014/0342373 A1 Nov. 20, 2014

Related U.S. Application Data

(60) Provisional application No. 61/536,132, filed on Sep. 19, 2011.

(51) Int. Cl.
*B01L 3/00* (2006.01)
*G01N 33/543* (2006.01)
(Continued)

(52) U.S. Cl.
CPC .. *B01L 3/502784* (2013.01); *G01N 33/54333* (2013.01); *B01L 2200/0673* (2013.01);
(Continued)

(58) Field of Classification Search
None
See application file for complete search history.

(56) References Cited

U.S. PATENT DOCUMENTS

2008/0003142 A1\* 1/2008 Link ............... B01F 3/0807
422/82.08
2008/0302732 A1\* 12/2008 Soh ............... B01L 3/502761
210/695
(Continued)

FOREIGN PATENT DOCUMENTS

EP 2 078 952 A2 7/2009
WO 2009/140373 A2 11/2009
WO 2010/042637 A2 4/2010

OTHER PUBLICATIONS

International Search Report and Written Opinion dated Dec. 17, 2012, issued in corresponding International Application No. PCT/IB2012/053766, filed Jul. 24, 2012, 10 pages.
(Continued)

*Primary Examiner* — Erik B Crawford
(74) *Attorney, Agent, or Firm* — Christensen O'Connor Johnson Kindness PLLC

(57) ABSTRACT

The present invention concerns a microfluidic system comprising: a microchannel containing several elements of two non-miscible fluids, the microchannel comprising a droplet (30) containing magnetic particles (M), and a device for generating inside the microchannel magnetic field, said device comprising an activable magnetic element, the activable magnetic element comprising a tip (5,6), the microfluidic system being configured to transport the droplet by flow or by pressure difference.

23 Claims, 8 Drawing Sheets

(51) Int. Cl.
    *H01F 21/06*     (2006.01)
    *H01F 1/44*     (2006.01)

(52) U.S. Cl.
    CPC ............... *B01L 2300/0654* (2013.01); *B01L 2300/0887* (2013.01); *B01L 2400/043* (2013.01); *H01F 1/447* (2013.01); *H01F 21/06* (2013.01); *Y10T 436/255* (2015.01)

(56) References Cited

U.S. PATENT DOCUMENTS

| | | | |
|---|---|---|---|
| 2009/0220979 A1* | 9/2009 | Davis | G01N 33/54333 435/6.13 |
| 2009/0235990 A1* | 9/2009 | Beer | B01F 3/0807 137/3 |
| 2009/0325192 A1* | 12/2009 | Kirakossian | B01L 3/508 435/7.2 |
| 2010/0308945 A1 | 12/2010 | Zantl | |
| 2011/0076692 A1* | 3/2011 | Sista | G01N 33/54366 435/7.4 |
| 2011/0311980 A1* | 12/2011 | Pollack | B01L 3/502761 435/6.12 |

OTHER PUBLICATIONS

Tsuchiya, H., et al., "On-Chip Polymerase Chain Reaction Microdevice Employing a Magnetic Droplet-Manipulation System," Sensors and Actuators B: Chemical 130(2):583-588, Mar. 2008.

* cited by examiner

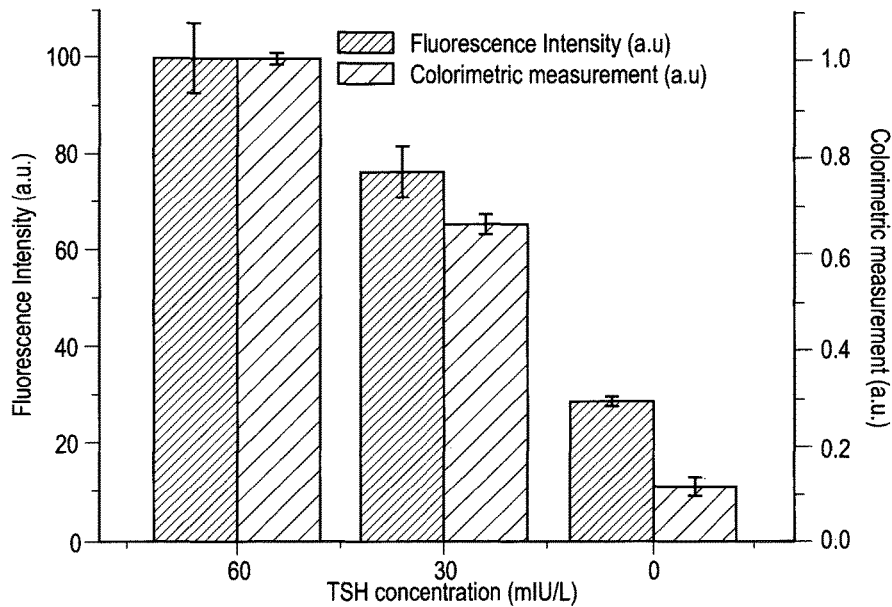

Fig. 7

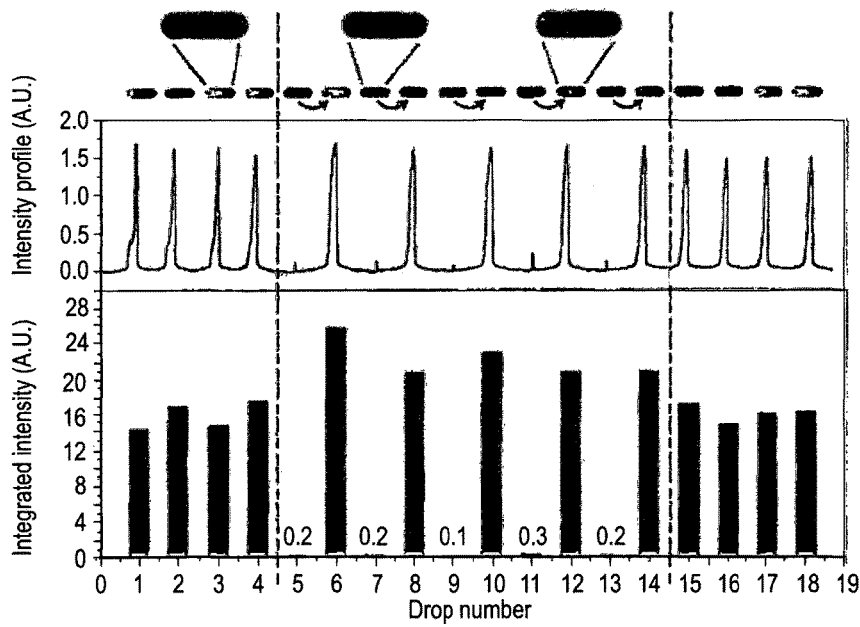

Identical droplets train containing 0.8µg fluorescent beads is initially produced from a 10mg/mL beads solution. Beads are transferred from a droplet to the following one (narrow). Three families of droplets appear: (I) the ones with their initial quantity of beads, (II) the ones in which beads were captured, and (III) the ones containing their initial quantity of beads and the released particles from the previous drop (A). The fluorescence profile is measured (B) and integrated (C).

Fig. 8

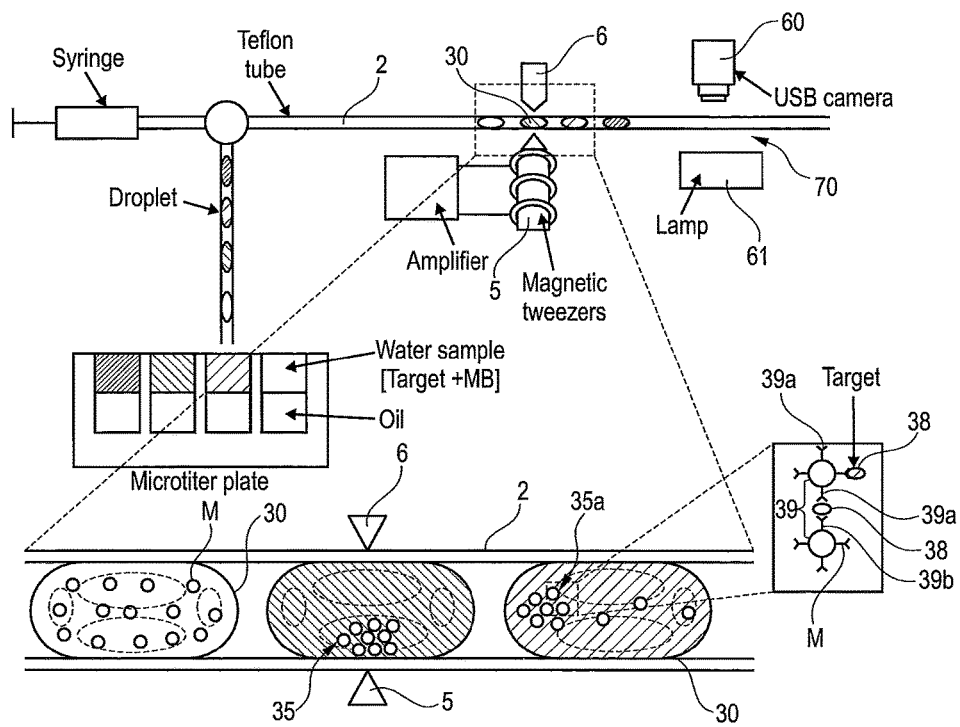
Fig. 9
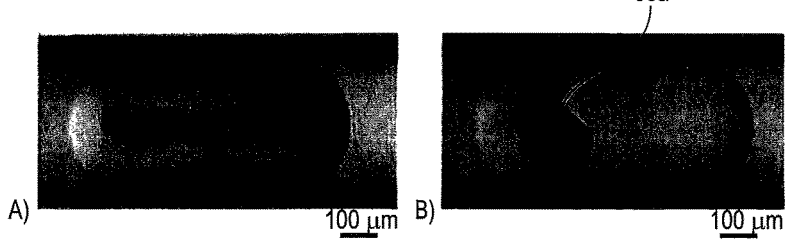
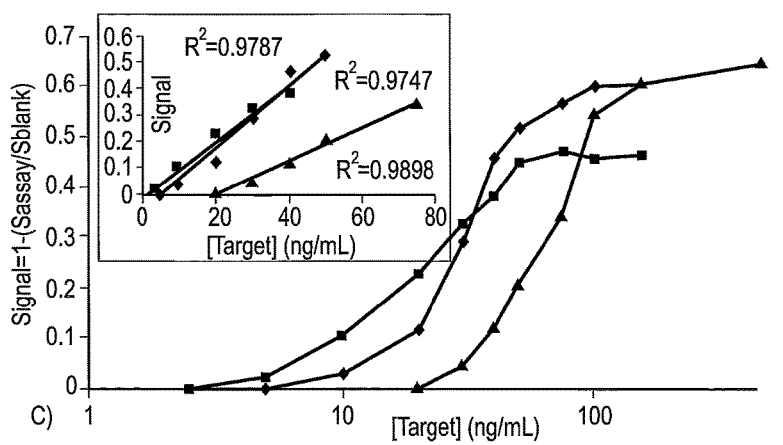
Fig. 10

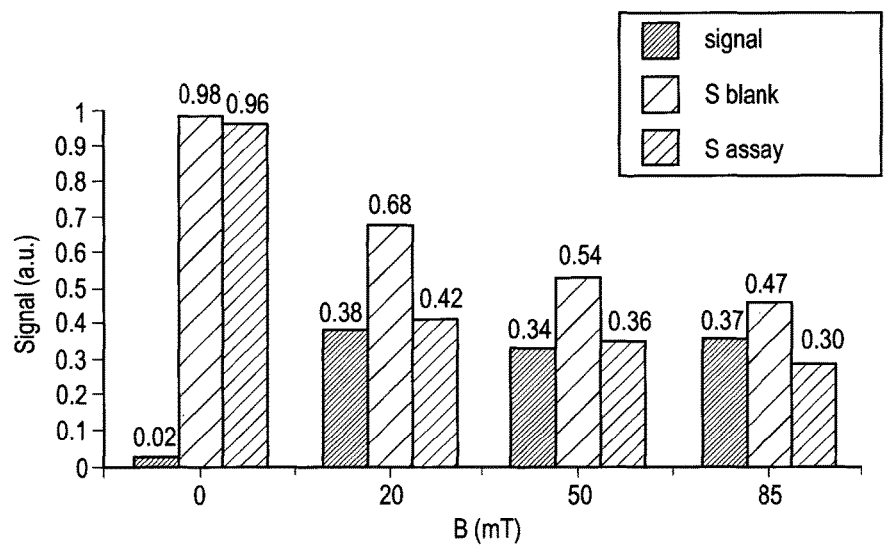
Fig. 11
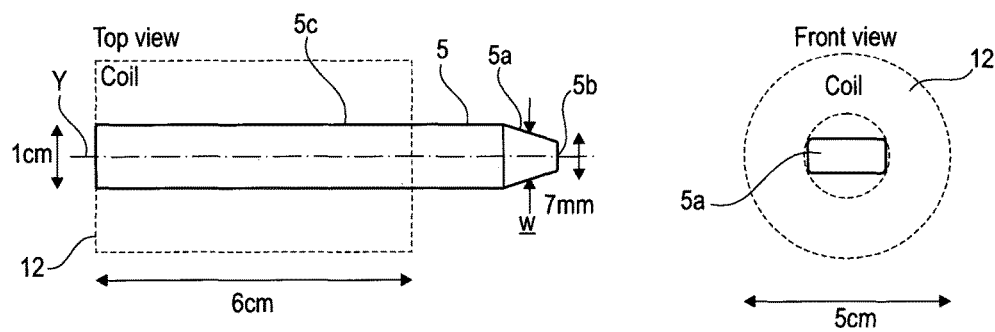
Fig. 12
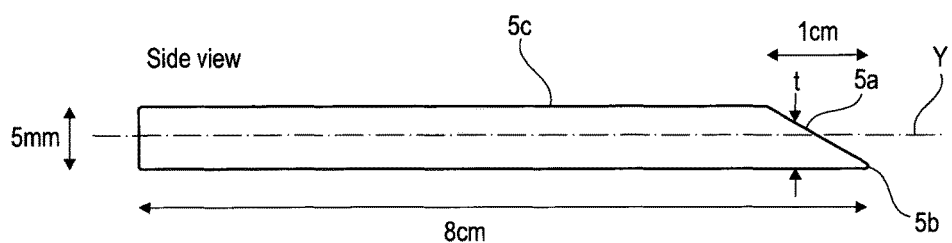
Fig. 13
Fig. 14

MICROFLUIDIC SYSTEM

The present invention relates to microfluidic devices and methods, in particular, intended to magnetically manipulate magnetic particles and their applications in detection and/or quantification of analytes.

BACKGROUND

Immunoassay is a powerful technique extensively used in clinical research and medical diagnosis for diseases biomarker screening. Its remarkable specificity and sensitivity is due to the molecular recognition between an antibodies and its target among a huge range of material in a sample. Most of assays are heterogeneous: the immunologic complex is created onto a solid surface, typically the bottom of micro-titer plate, and unbound molecules are removed by several washing step before detection. However, this format presents several drawbacks in which the low capture area and surface-to-volume ratio are the most crucial because they are directly related to the immunoassay sensitivity.

The apparition of magnetic micro-particles as solid support to perform biomarker capture enables to overcome one of those issues. Micrometric beads show a large specific surface with an important binding capacity giving a better capture efficiency. Moreover, thanks to their superparamagnetic property, they are easy to handle what makes the numerous immunoassay separation and washing steps faster to perform. The coupling of the large capture area with the increase in reaction time due to the microfluidic format enables to achieve point-of-care platform detecting biomarker in few minutes with a good sensitivity.

Immuno-agglutination is one of the simplest and fastest one-step immunoassays. It consists in creating aggregates using functionalized beads in the presence of a target with at least two binding sites [15]. This simple procedure is widely applied to immunodiagnostics but it still limited by the slow kinetics of aggregates formation. Several strategies based on microfluidics have shown the possibility to reduce reaction time and improve sensitivity but the procedures remain laborious [16].

Currently, most of beads-based ELISA performed in microfluidic are carried out in continuous flow but for handling and pumping reasons the liquid volumes cannot be lower than few microliters. Reducing the volume of immunoassays is required for some clinical application where the volume sample is available in really small quantity such as new born blood samples. Also, reducing sample or reagent volume is critical for applications in which a multiplicity of criteria or materials or samples have to be screened, as the case in drug screening, high throughput screening, combinatorial chemistry, systems biology, digital biology, synthetic biology, and the like. The screening of neonatal diseases is already developed in most of countries (Clague & Thomas, 2002) [5] but sub-microliter reactions on those samples could give the opportunity to perform multiple analyses from the same sample volume taken. The droplet microfluidic enables to handle small self-enclosed volumes. However, multistep reactions are not easy to execute with usual droplet manipulations such as merging and splitting that is why magnetic droplet handling offers an easy way to overcome those issues and to perform bead-based assays on digital microfluidic platform.

Several methods have been used to manipulate magnetic particles in order to do bio-analytical in an integrated system. First, Shikida et al. (Shikida et al., 2006a) (Shikida et al., 2006b) [6] and [7] introduced beads transfer between two water droplets dispersed in oil in a microfluidic system. The extraction is performed by splitting a small droplet containing particles thanks to a moving magnet and gating structures to retain the drop during extraction. The drop volume had been reduced from about 40 to few microliters in order to perform PCR amplification (Tsuchiya et al., 2008) [3]. Based on this work, many examples of magnetic beads manipulation was demonstrated on digital microfluidic. Most of them are 2D platform which can be divided in two groups: the one where beads are extracted from drops deposed onto a surface with a mobile magnet (Zhang et al., 2010) [8] (Long et al., 2009) [9] and the one based on electro-wetting device in which droplets are moved close to a fixed magnet (Sista et al., 2008) [1]. Although all these systems are able to perform multiple step assays, they are not simple and easy-to-operate mostly due to the droplet creation and positioning onto the surface and/or the magnet movement to implement. Lehmann et al. (Lehmann et al., 2006) [10] reported a platform integrating an array of coils on a PCB substrate coupled with a hydrophobic/hydrophilic surface patterning to split drops. Despite of this integration, the system complexity is highly increased and drop volumes and beads amount are still in the microliter and hundreds of micrograms range.

Biphasic microfluidics offer unique capabilities for the development of flexible and high throughput analytical systems. Platforms combining droplet microfluidics with magnetic particles provide the advantages of heterogeneous assays, while enabling complex operations such as on-chip transport without dispersion, mixing and merging of aliquots. Interesting applications based on this strategy were proposed, using in particular electrowetting on 2D supports [1], but they are relatively low-throughput, and electrowetting raises delicate contamination issues limiting bioassays performances.

It is thus an object of the invention to overcome the above limitations. In particular, in one of its aspects, the invention relates to a microcapillary or microchannel based platform with integrated magnetic tweezers enabling the fast and robust implementation of complex bead-based bioassays in liquid droplets. This approach thus enables us to split, transport, mix and merge droplets reliably while providing high throughput analysis and multiplexing capabilities that are necessary to perform bioassay.

Further, the methods disclosed e.g. in Gu et al., Anal chem, 2011, dx.doi.org/10.1021/ac201678g, may not provide the separation of superparamagnetic particles, without combining said superparamagnetic particles with ferromagnetic particles.

The latter particles, however, do not separate easily after having been magnetized, so this approach of the prior art did not allow resuspension, and strongly limited the number of steps of protocols. These disadvantages might be shared by ferrimagnetic particles, or by antiferromagnetic ones.

In addition, prior droplet systems, may not provide the possibility to perform washing and elution steps.

In other known methods [12], droplets were split by hydrodynamic means, and a magnet was used to move magnetic particles preferentially in one of the daughter droplets. However, in this case the droplet containing the particles and the other have a comparable size, so the separation power is poor.

It is another object of the invention to increase aggregate formation kinetics, reduce volumes and provide a fully automated and low cost platform for immuno-agglutination.

It is an object of the invention, to provide a method for performing chemical, biological, physical or biochemical processes, analysis or reactions, thanks to an improved extraction process.

It is an object of the invention to provide improved methods for performing chemical, biological, physical or biochemical processes, analysis or reactions, wherein superparamagnetic particles are contained in droplets contained in a microchannel.

It is an object of the invention to provide a system that allows to stop magnetic particles contained in a droplet, into a secondary droplet containing a minimal volume of fluid, without stopping the remainder of the droplet.

It is an object of the invention to provide systems for performing various types of assays, optionally comprising several steps, in microfluidic devices that may not comprise microelectrode arrays or microfabricated microcoils.

It is an object of the invention to provide systems for performing various types of assays, optionally comprising several steps, in microfluidic devices wherein droplets are transported by flow or by a pressure difference.

SUMMARY

According to a first of its aspects, the present invention concerns a microfluidic system comprising:
- a microchannel in particular comprising a longitudinal axis, and
- a device for generating inside the microchannel a magnetic field, said device comprising an activable magnetic element.

By an "activable magnetic element", we mean a material that can be reversibly magnetized, so that it can induce around it a magnetic field. Typically, a directly activable magnetic element is the core of an electromagnet.

An activable magnetic element according to the invention can be indirectly activable. An example of an activable magnetic element is an element of a soft magnetic element, included in a mechanical device in which a permanent magnet can be reversibly brought in close proximity of a portion of said soft magnetic element by mechanical means in which a permanent magnet rotating around an axis can be rotated in order to have is pole in contact with one side of the core, in such case the core is activated, or rotated in order to be no more in contact with such core, in such case the core is unactivated.

In a preferred embodiment, the activable magnetic element comprises a tip.

In a preferred embodiment, the active magnetic element comprises a core and a tip.

For the sake of description, we may distinguish in the description the "core" of the magnetic element, which is a relatively bulky piece of magnetic material, with a section significantly larger than that of the tip, and the tip.

In a preferred embodiment, the tip is an integral part of the magnetic element. In other preferred embodiments, the tip may be constituted by a magnetizable material, magnetically connected to the core of the magnetic element, so that the field lines created in said core propagate into said tip.

By tip, we mean one extremity of a solid material, which has a convex shape, and a sectional area which decreases along an axis of the tip.

The tip may have a sectional area, as measured transversely to the longitudinal axis, that decreases along this longitudinal axis.

This decreasing section may create a convergence of magnetic field lines inside said tip, and thus may increase the absolute value of the magnetic field at the tip, while concentrating the field on a small volume only.

This combination of small size and high magnetic fields may allows to create stronger magnetic field gradients, as compared to e.g. the cylindrical or rectangular magnets of previous art.

Another example of an indirectly activable element is a piece of a soft magnetic material with a tip facing one of the poles of another directly activable or indirectly activable magnetic element. In other preferred embodiment, said magnetic element comprises a core which can be reversibly magnetized and a tip magnetically coupled to the core.

For instance, in a preferred embodiment, said core can be surrounded by a conducting coil, connected to a current generator.

In some preferred embodiments, particularly useful for implementing complex protocols, microfluidic systems of the invention may comprise several of the said activable magnetic elements, located upon several different areas of a microchannel, or on several different microchannels of the microfluidic system.

In a particularly preferred embodiment, the system comprises at least a pair of activable magnetic elements which face each other across the microchannel.

In another preferred embodiment, the pair of facing magnetic elements can comprise a directly activable magnetic element and a second indirectly activable one, which is "slave" to the first.

By this, we mean that the second magnetic element is a magnetizable material with a tip facing the tip of the first magnetic element across the microchannel, and only acquiring its magnetization by induced magnetization from the first one.

This configuration has the advantages of a pair of magnetic elements, without the cost of having for instance two coils.

In another preferred embodiment according to the invention, the system may comprise a plurality of activable magnetic elements located at various locations on the length of a same microchannel.

Thanks to this, magnetic field lines may be better localized, and magnetic field gradient may be stronger.

Introducing several magnetic activable elements along the length of the same microfluidic channel may allow the performing of complex operations between droplets.

It may, in particular, offer the opportunity of transferring magnetic particles to one droplet with a first pair of magnetic activable elements, wait for incubation while the droplet is still moving and extract the incubated magnetic particles using a second pair of magnetic activable elements. The particles can thus be incubated, washed as many times as needed.

It may also be possible of inverting the direction of droplet motion to bring back a droplet in the same pair of magnetic activable elements.

The present invention may advantageously provide methods wherein droplet motion is completely decoupled from particle handling.

According to another preferred embodiment, the same microchannel, or several microchannels, can be located in front of a single magnetic element, or between the two elements of a pair of magnetic elements.

This may allow to have several active zones inside a microchannel or inside a microchannel array, with the cost and complexity of only one activable magnetic structure. One way of performing this is to use one or two bladelike magnetic elements, with a microfluidic system comprising several microchannels, or a serpentine microchannel, or alternately, several tubings or a single tubing folded into a coil in order to pass several times in the vicinity of the tip(s).

The system according to the invention advantageously comprises a microfluidic device configured to create in the microchannel a sequence of several elements of at least two non-miscible fluids.

Typically, such sequences can be droplets of a first fluid in a surrounding immiscible second fluid. Said first fluid can be either aqueous, in such case said second fluid is either an oil (fluorinated or non-fluorinated), or air, or any fluid non miscible with water. Obviously, said first fluid may also be a fluid non miscible with water, and said second fluid be aqueous, or another fluid non miscible with water, or the second fluid may be a non aqueous fluid non miscible with the first, e.g. hydrogenated oil and fluorinated oil, or any other combination of non miscible fluids.

In a particularly advantageous embodiment, said first fluid is aqueous, and said second fluid is a fluorinated oil.

For definiteness, we shall call "droplet" any kind of bolus of a fluid surrounded by another immiscible fluid, whatever its shape: it can be for instance a floating droplet, or a droplet highly confined by its container, sometimes called in the literature "plug" or "slug".

Also, by extension, the term "droplet" here will encompass any compartmentalized portion of fluid able to contain magnetic particles, suspended in a fluid in which it can propagate without diffusion. For instance, it encompasses vesicles or microcapsules.

According to a preferred embodiment, the magnetic particles used in the system according to the invention are surface-functionalized.

Each of the surface-functionalized magnetic particles may provide at least one binding site, preferably at least two binding sites, for a target, the target e.g. being present in the droplet containing the surface-functionalized magnetic particles.

The binding sites may comprise an element chosen among the following list: antibodies, antigens, metals, histidine tags, hydrophobic moieties, hydrogen-binding moieties, protein A, ligands based on nucleic acids, and able to bind specifically to some nucleotidic sequences, polyelectrolytes, phospholipids, chemicals, drugs, nucleic acids, combinations of nucleic acids and enzymes, such as mixtures used for DNA amplification, fluorescent moieties, luminescent moieties, dyes, nanoparticles, gold nanoparticles, quantum dots, DNA intercalating dyes, aptamers, or any types of species putatively able to affect the metabolism of cells, or the properties of colloidal objects in particular their optical properties, catalysts, or enzymes, capable of modifying a compound, or a mixture thereof, the binding sites preferably comprising an antibody and the target the associated antigen or vice versa.

The target may be captured on the binding sites of the surface-functionalized magnetic particles.

The magnetic particles may form an aggregate when used in a system according to the invention.

By "aggregate of magnetic particles", it is meant a plurality of magnetic particles linked to each other or in contact with each other.

The magnetic particles forming the aggregate may be linked to each other by a linking bridge having the following structure: binding site of a first magnetic particle-target-binding site of a second magnetic particle different from the first.

The magnetic particles may form an aggregate while a magnetic field created by the activable magnetic element is applied.

The magnetic particles may also form an aggregate whereas they are not submitted to a magnetic field created by the activable magnetic element.

Indeed, the presence of linking bridges between different magnetic particles advantageously allows to keep magnetic particles under an aggregated form even in the absence of magnetic field created by the activable magnetic element.

The ratio (mass of magnetic particles in the droplet)/(volume of the droplet containing the magnetic particles and optionally the target) may be comprised between 0.1 mg/mL and 10 mg/mL and/or the ratio (mass of target in the droplet)/(volume of the droplet containing the magnetic particles and the target) may be comprised between 10 ng/mL and 1000 ng/mL.

The droplet containing the magnetic particles may be a water-in-oil droplet.

In an embodiment, the microchannel contains a plurality of droplets containing magnetic particles.

According to another of its aspects, the present invention concerns an assembly comprising:
 a system as defined above, and
 a detector configured to measure at least one characteristic of a droplet containing magnetic particles present in the microchannel, said droplet preferably comprising an aggregate of magnetic particles.

The detector may be an optical detector and may be configured to measure at least one optical characteristic, preferably optical transmittance, of the droplet.

The assembly may further comprise a light source configured to irradiate the droplet, the optical detector e.g. being configured to measure the quantity of light from the light source absorbed by the droplet.

The invention also concerns, according to another aspect, a method of extracting at least one magnetic body from a first primary droplet of a first fluid flowing in a microchannel, said method preferably using a system as defined above, and comprising:
 capturing the magnetic body in the vicinity of at least one activable magnetic element by submitting the magnetic body to a magnetic field generated by the activable magnetic element,
 deforming the first primary droplet,
 splitting the first primary droplet into a first secondary droplet and a second secondary droplet, the first secondary droplet comprising the magnetic body and remaining captured by the magnetic field in the vicinity of the activable magnetic element to extract the at least one body from the first primary droplet.

The magnetic force leading to particle capture and extraction may be function of both magnetic field intensity and magnetic field gradient.

According to another of its aspects, the present invention also concerns a method of manipulating at least one magnetic body comprising:
 extracting the magnetic body from a first primary droplet of a first fluid flowing in a microchannel according to the method as defined above, and
 releasing the magnetic body by modifying the intensity and/or gradient of, in particular stopping, the magnetic field created by the activable magnetic element.

According to another of its aspects, the invention concerns a method of manipulating magnetic particles, the method preferably using a system or an assembly as described above, comprising:

capturing and aggregating magnetic particles contained in a droplet in the vicinity of at least one activable magnetic element by submitting the magnetic particles to a magnetic field generated by the activable magnetic element, preferably an activable microfluidic element excited by a coil, the magnetic particles being surface functionalized, each of the surface-functionalized magnetic particles providing at least one binding site, preferably at least two binding sites, for a target, the target being present in the droplet containing the magnetic particles.

Such method advantageously increases aggregate formation kinetics, reduces volumes and provides a fully automated and low cost platform for immuno-agglutination.

The target may be captured on the binding sites of the surface-functionalized magnetic particles, preferably before the end of the capturing and aggregating step, more preferably before the beginning of this step.

The magnetic particles forming the aggregate may be linked to each other by a linking bridge having the following structure: binding site of a first magnetic particle-target-binding site of a second magnetic particle different from the first.

The ratio (mass of magnetic particles in the droplet)/(volume of the droplet containing the magnetic particles and the target) may be comprised between 0.1 mg/mL and 10 mg/mL and/or the ratio (mass of target in the droplet)/(volume of the droplet containing the magnetic particles and the target) may be comprised between 10 ng/mL and 1000 ng/mL.

The droplet containing the magnetic particles may be a water-in-oil droplet. The flow rate of the droplet in the microchannel is preferably lower than 1 µL/minute.

The duration of the capturing step may vary depending on the time necessary for incubation of the sample and the particles. It may be comprised between 0.1 s and 1 h, preferably between is and 30 nm, more preferably between 10 s and 10 nm. Preferably, the aggregation step is shorter than the capture step, and related to the passage of one droplet in front of the magnetic trap. It may be comprised between 0.01 s and 100 s, preferably between 0.1 s and 10 s, or between 0.3 s and 2 s. The method may further comprise a step of releasing the aggregate of magnetic particles by modifying the intensity and/or gradient of, in particular stopping, the magnetic field created by the activable magnetic element.

In an embodiment, the magnetic particles still forms an aggregate after the releasing step.

In an embodiment, the droplet may be flown to a detection zone after the releasing step wherein a characteristic of the droplet is measured, the droplet still comprising an aggregate of magnetic particles during this measurement.

During this measurement, the magnetic particles forming the aggregate may be linked to each other by a linking bridge having the following structure: binding site of a first magnetic particle-target-binding site of a second magnetic particle different from the first.

The characteristic may be an optical characteristic, preferably optical transmittance, of the droplet.

In an embodiment, a light source irradiates the droplet while it is present in the detection zone, the quantity of light from the light source absorbed by the droplet being measured in the detection zone.

A plurality of droplets containing magnetic particles may be present in the microchannel.

In an embodiment, the method further comprises a demagnetization step of the activable magnetic element performed by inducing an alternative current with an intensity decreasing with time in the conducting coil, said intensity being in particular decreasing down to 0.

The activable magnetic element may have a tip of a thickness, measured along the longitudinal axis of the micro channel, less than a length of the droplet, preferably by a ratio of less than 1:5, most preferably of less than 1:10.

The microfluidic system may be configured to transport the droplets by flow or pressure difference.

The flow or pressure difference may be generated by a pump or any other devices known as suitable by the skilled artisan.

The microfluidic system may comprise a pressure sensor and/or a pressure controller. In an embodiment, the microfluidic system comprises a sensor allowing measuring the velocity of the flow and/or a controller to control such velocity.

Magnetic Element

Tip Shape

The simplest example of a tip is a cone with a circular section. Conical tips according to the invention preferably have an half angle at summit smaller than 45°.

Another type of tip particularly useful in the invention, is a blade-like tip.

In that case, of course the tip has an acute tip angle in one direction only, i.e. in a plane perpendicular to the edge of the blade. Blade-like tips according to the invention preferably have a tip angle smaller than 45°.

However, tips according to the invention may have many different shapes.

For instance, the three dimensional shape of the tip may have more complex shapes involving ellipsoids, rounded blades and the like.

Also for reasons of mechanical fabrication or solidity, tips according to the invention may be blunt of flat at its very end. However, as explained above, it is advantageous that they still have a generally decreasing section.

The flat or blunt part may only represent a small area as compared to the largest section of the tip, typically smaller than 10% of said largest section, preferably less than 5% of said largest section, and more preferably less than 2% of said largest section.

When technically possible, however, the tip may advantageously have no blunt of flat end.

In an embodiment, the tip has a longitudinal axis transverse to the longitudinal axis of the micro channel, in particular perpendicular to the longitudinal axis of the micro channel.

In an embodiment, when moving towards the micro channel, the section of the tip decreases on all or part of its length.

Tip Size

The typical dimensions of the tip may vary depending on the applications, and notably on the size of the microchannel.

For the sake of terseness and definiteness, except if stated otherwise, by "size of the tip", we shall mean dimension along the plane in which the convergence angle of the tip is smallest. For instance, for a bladelike tip, dimensions will be considered in a plane perpendicular to the blade edge.

By "radius of gyration of the tip", we shall also mean, except if otherwise stated, the effective radius of gyration in the plane in which the convergence angle of the tip is smallest.

We use the term "effective", because for technical reasons the tip may not be perfectly circular, it may as stated above have a small blunted part, or some irregularities, and in that case the effective radius of gyration is the radius that would have a smooth fraction of circle most closely encompassing the end of the tip.

The tip of the magnetic element may have dimensions comparable with the dimensions of the microchannel.

By "dimensions of the microchannel", except when stated otherwise, we shall mean its dimension along the line defined by the shortest distance between the tip and the microchannel. Obviously, if the microchannel is cylindrical, its dimension is its diameter. If it has a rectangular section, by dimension we mean its thickness counted perpendicular to the tip axis.

Another advantage of the invention, is that the magnetic elements can be activated by "macrocoils", that can be placed at a distance from the microchannel itself. Thus, heating problems are minimized, higher currents can be used, and a stronger magnetic force can be created than prior art as described e.g. in EP 1974821 to Gijs, or in WO200361470 to scherrer. It is thus an object of the invention, to provide a microfluidic system comprising a microchannel, means to create in said microchannel a sequence of several elements of at least two non-miscible fluids, and at least one activable magnetic element with a tip facing said microchannel, wherein said tip is in magnetic connection with a magnetic core, wherein said magnetic core has a section significantly larger than said channel, and significantly larger than the radius of gyration of said tip.

Magnetic Field Created

It is thus another aim of the invention, to provide microfluidic systems with at least a microchannel and an activable magnetic element, which may create in a portion of said microchannel a magnetic field intensity comprised between 10 mT and 1 T and preferably between 20 mT and 100 mT.

It is thus another aim of the invention, to provide microfluidic systems with at least a microchannel and an activable magnetic element, which may create in a portion of said microchannel a magnetic field gradient, in particular along the longitudinal axis of the microchannel, comprised between 10 and 10000 T/m, more preferably between 100 T/m and 200 T/m, more preferably between 200 and 500 T/m, or between 500 and 1000 T/m.

The magnetic field may be continuous or alternative, in particular sinusoidal.

Micro-Channels

Also, it should be noted that "microchannels" as defined in the invention may advantageously be prepared by lithography or "soft lithography" methods, but we also designate by this term any tubular like container or duct, e.g. rigid or flexible tube.

However, as opposed to most droplet magnetic manipulation devices of prior art, which involved two dimensional planar arrays, microchannels according to the invention are preferably unidimensional, e.g. they have a width, a thickness and length, and the length is much larger, at least 10 times, and often 100 times or more, larger than said width and thickness.

Besides this, they are advantageously cylindrical or parallelipedical, but they may also have more complex shapes, involving wedges, bulges, recesses, microstructures on their walls, or any features that can be interesting in microfluidics.

As a general feature, however, microchannels of the invention are of submillimeter section, i.e. they have either a cross section smaller than 1 mm$^2$ on at least a portion of their length, in particular on at least the portion of their length which faces the magnetic activable element, in particular on at least 50% of their length, or at least one cross sectional dimension smaller than 500 µm.

In different preferred embodiments, the cross section of the microchannels according to the invention is comprised between 100 µm$^2$ and 1000 µm$^2$, or between 1000 µm$^2$ and 10 000 µm$^2$, or between 0.01 mm$^2$ and 0.1 mm$^2$ on at least a portion of their length, in particular on at least the portion of their length which faces the magnetic activable element, in particular on at least 50% of their length, in particular on the totality of their length.

The microfluidic systems according to the invention comprises at least one microchannel and may comprise several microchannels. Said microchannels can be fully linear, or branched into a network. Thus, although mostly linear, microchannels within the invention, may comprise branchings such as side branchings, or cross branchings. Preferably, the branching areas are located along the microchannel in areas distant from the areas facing the activable magnetic elements.

Droplets in the Microchannel

Droplets Size and Production

The size of the plugs or droplets can be very variable, ranging e.g. from 1 picoliter (pL) to 2 L.

However, the invention may advantageously allow the obtaining of droplets in ranges of size not easily available in prior art, in particular between 10 pL and 500 nL, in particular between 10 pL and 100 pL, between 100 pL and 1 nL, between 1 nL and 10 nL, between 10 nL and 100 nL, or between 100 nL and 500 nL.

Various means to create in the microchannel a sequence of several elements of at least two non-miscible fluids are known in the art.

They can for instance involve flow focusing devices (Anna et al. Applied Physics Letters, 82, p 384, 2003 (DOI 10.1063/1.1537519); T-junctions (Zheng et al., Analytical Chemistry, 2004, 76, 4977-4982), or two-phase micropipetting (Chabert et al, Analytical Chemistry, 2006, 78, 7722-30 7728), or a combination of such.

Thanks to this and combined to the globally unidimensional nature of the microchannel, the invention may allow to transport a multiplicity of samples or reagents, in the form of plugs or droplets, by a simple flow or pressure of the surrounding fluid.

This alleviates the need for integrating into the microsystem microcoils, as in prior art by Elsenhans, Gijs et al (e.g. EP1974821) or microelectrodes as e.g. in Pamula et al. (WO 2010/042637).

Magnetic Particles Contained in the Droplets

The magnetic particles are preferably superparamagnetic.

The size of the magnetic particles may be very diverse.

By size of a particle, it is meant the greatest dimension of said particle.

In a preferred embodiment, the particles have an average size comprised between 0.5 µm and 5 µm.

The average size of a set of particles is, unless otherwise specified, the granulometric statistic size at D50.

In another embodiment, the magnetic particles comprise a first set of particles with an average size comprised between 1 µm and 5 µm, and a second set of particles mixed with the first set, with a greater average size, preferably between 10 and 50 µm, or between 50 and 100 µm, or between 100 and 200 µm, or between 200 and 500 µm.

As regards the mass of magnetic particles, it can also vary within the invention, but typically the invention is advantageous for manipulating small masses of particles. Typically, the mass of magnetic particles contained in one droplet will be comprised between 0.5 µg and 2 µg, or between 2 µg and 8 µg.

In some other embodiments, requiring high magnetic field gradients and small microchannels, with at least one dimension smaller than 50 µm, the mass of magnetic particles may be comprised between 0.01 µg and 0.1 µg, or between 0.1 µg and 0.5 µg. Alternately in other embodiments, involving microchannels with at least one lateral dimension larger than 100 µm, or even larger than 300 µm, the mass of magnetic particles can be comprised between 8 µg and 100 µg.

Numerous types of superparamagnetic particles are known by those in the art and can be used in the invention. Notably, the invention is particularly advantageous with particles bearing ligands.

As used herein, ligand represent a species, or a function, able to bind reversibly or irreversibly with another species, in particular an analyte. Numerous ligands are known from those skilled in the art. Of particular interest as ligands within the invention are antibodies, e.g. antibodies directed towards surface antigens of the COI. However, numerous other ligands can be used, such as metals, histidine tags, hydrophobic moieties, hydrogen-binding moieties, protein A, and the like. Other types of ligands useful in the invention are ligands based on nucleic acids, and able to bind specifically to some nucleotidic sequences. Ligands within the invention, such as e.g. polyelectrolytes, or phospholipids, can also exert their binding thanks to electrostatic interactions.

Ligands may also represent chemicals, drugs, nucleic acids, combinations of nucleic acids and enzymes, such as mixtures used for DNA amplification, antibodies, fluorescent moieties, luminescent moieties, dyes, nanoparticles, gold nanoparticles, quantum dots, DNA intercalating dyes, aptamers, or any types of species putatively able to affect the metabolism of cells, or the properties of colloidal objects according to the invention, in particular their optical properties.

In other embodiments, magnetic particles of the invention may bear attached to their surface catalysts, or enzymes, capable of modifying a compound.

This way the invention may be used to perform, in extremely small volumes, all kind of reactions, notably ELISA, nucleic acid amplification, sequencing reactions, protein digestion, or chemical reactions, notably catalytic reactions.

Methods and Applications

In some preferred embodiments, said several activable elements can be activated simultaneously.

In yet more preferred embodiments, though, at least some of them can be activated independently, in order to widen the flexibility of the protocols.

In particular, an activable element will advantageously be activated upon the passage of one droplet containing magnetic particles, in order to retain said magnetic particles.

Oppositely an activable magnetic element car be deactivated upon the passage of a droplet, in order to let the droplet pass with its content unaltered, or in order to release into said droplet, a secondary droplet containing magnetic particles previously retained by said activable magnetic element.

Interestingly, said activation and deactivation can be performed either manually, automatedly or on demand.

Interestingly, it may be synchronized with the displacement of the droplets. In that case, the position of the droplet in the vicinity of one or several activable magnetic elements can be detected by different means, for instance optical means, by a magnetic sensor, or by an impedencemetry. This detection signal is then fed to an automated system, for instance a software in a computer. Preferably, said software is able to activate or deactivate the magnetic elements in response to said signal. In other embodiments, that may advantageously be combined with the above, said software may also control the motion of the carrier fluid transporting the droplets in the microchannels.

In the methods according to the invention, a first primary droplet containing magnetic particles may be split into a first secondary droplet containing a major part of said magnetic particles and a minor part of the fluid contained in said first primary droplet, and a second secondary droplet, containing a minor part of said magnetic particles and a major part of the fluid contained in said first primary droplet.

Preferably, said second secondary droplet is carried out with the flow, and said first secondary droplet remains in front of the magnetic tip.

Preferably, said second secondary droplet contains between 20% and 10%, or between 10% and 5%, or between 5% and 2%, or between 2% and 0.5%, or less than 5%, of the magnetic particles contained in said primary droplet.

Preferably, too, said first secondary droplet contains between 20% and 10%; or between 10% and 5%, or between 5% and 2%, or between 2% and 0.1%, of the volume of fluid initially contained in the primary droplet.

Another advantage of the invention, is that thanks to the activable nature of the magnetic elements, it also allows to release the magnetic particles trapped in the above first secondary droplet, into a second primary droplet of a larger volume.

It is thus another object of the invention, to provide a method for performing chemical, biological, physical or biochemical processes, analysis or reactions, thanks to a resuspension process where magnetic particles trapped in a first secondary droplet, are released into a second primary droplet with a volume larger than the volume of said first secondary droplet.

Preferably, too, the volume of said first secondary droplet is comprised between 50% and 20%; or between 20% and 10%; or between 10% and 5%, or between 5% and 2%, or between 2% and 0.1%, of the volume of said second primary droplet.

Advantageously, too, the invention provides means to efficiently mix said magnetic particles in said second primary droplets. Said means may selected among a simple use of convective flow in the droplet, improvement of this flow by bends in the microchannel, or by microstructures in the microchannel, or by sound or ultrasound waves, or by flow or pressure pulsation, or by an uneven diameter of the microchannel, as a non exhaustive list.

Obviously, it is also a particular advantage and object of the invention, to provide methods for performing chemical, biological, physical or biochemical processes, analysis or reactions, wherein several of the above steps of extraction and/or resuspension are combined within the same microfluidic system.

This is advantageously performed in microsystems comprising magnetic elements of the invention facing several different locations in the microfluidic system.

As another privileged embodiment, such methods can be performed by moving droplet back and forth droplets in a microchannel facing one or several magnetic elements of the invention. Depending on the orientation of the field generated in each tip, the combination of two active tips can be used either to capture and extract beads or to induce mixing in the droplet.

Acoustics waves, in particular ultrasounds, may propagate in the microchannel. Such approach could be used to improve mixing in the droplets. Nevertheless, a special care has to be taken to the possible heating effects induced by ultrasounds in the system.

In case of a remanent field would be observed in the tips, a simple demagnetization procedure can be performed by inducing an alternative current with a intensity decreasing with time in the coils (down to 0). Here is an example of a set of parameters that we used successfully:

Current intensity: linear decay 3 A→0 A
Frequency: 100 Hz
Sinusoidal/Square/wave signals were successfully used
Tip Material: mu metal or AFK502

The methods of the invention may be methods for detecting and/or quantifying an analyte in a sample.

It will be clear to those skilled in the art that the methods according to the invention may be used for microreaction, immunoreaction, enzymatic digestion, ELISA, diagnosis, prognosis, drug delivery, high throughput screening, and the like.

The methods of the invention can be applied to numerous types of analytes, biomolecules, polypeptides, proteins, metabolites, nucleic acids, cells, organelles, microparticles and nanoparticles, polymers, colloids, infections agents, food components, environmental samples.

The device of the invention can be integrated as a technological brick within more complex devices, in particular high throughput screening devices, lab on chips, point of care, laboratory instruments, robots, and the like.

Also, the methods of the invention can be integrated as part of complex protocols for diagnosis, drug discovery, target discovery, drug evaluation.

Of course, the microfluidic systems of the invention and the methods of the invention can be combined with, or comprise, all kind of microfluidic components or functions, known in the art.

Also, because of the small sizes of the samples used, the invention is particularly interesting for applications in cell assays, notably the screening of single cells, in digital biology, digital PCR, digital nucleic acid amplification.

By digital, we mean here biological operations that are made on a single copy of a biological or chemical object, as opposed to an ensemble of such objects, and in which the result of the operation on each of these single copies can be isolated.

By biological or chemical object, we mean any molecular, supramolecular, crystalline, colloidal, cellular, subcellular object, including as a non exhaustive list cellules, organelles, viruses, natural, artificial or modified DNA, RNA or nucleic acid mimics, proteins, glycoproteins, phosphoproteins, any substituted natural or artificial proteins, lipids, phospholipids, organic molecules, organometallic molecules, macromolecules, single crystals, quantum dots, nanoparticles, vesicles, microcapsules, and the like.

The invention is also advantageous for the manipulation or analysis of dangerous materials, for instance radioactive material, nanoparticles, toxic or explosive chemicals.

The invention may also be particularly useful in combination with various optical detection methods, and notably optical detection methods because by retaining magnetic particles in a secondary droplet, it is possible to reduce the optical absorption and noise created by these particles.

A non exhaustive list of applications are the enzymatic conversion of a substrate into a fluorescent product, luminescent detection, absorption detection, chemiluminescent detection, colorimetric detection, electrochemiluminescent detection.

The invention may also be used for detection methods based on magnetism, notably using magnetic sensors based on giant magnetoresistance or for protein cristallisation.

BRIEF DESCRIPTION OF THE DRAWINGS

FIGS. 5 to 8 show the results obtained by a method according to the invention, FIG. 9 diagrammatically represents the different steps of another bead-handling method according to the invention, FIG. 10 shows bright field micrographs of agglutination of magnetic beads in droplets, FIG. 11 shows the influence of intensity of the magnetic field on the method depicted in FIG. 9, and FIGS. 12 to 14 and 15 to 15F diagrammatically show details of variants of the microfluidic device that can be used in the methods according to the invention.

The extraction can be successfully performed with only one magnetic tip connected to an electromagnetic coil. Here is a schematic illustration describing the tip geometry (coil implantation in dashed line):

The materials used in our systems were mu-Metal or AFK502 or AFK01 (Arcelor Metal). We used a home made cylindrical electromagnetic coil composed of around 1000 turns of insulated copper wire (0.8 mm diameter). The current intensity used ranges from 0 up to 4 A.

A second tip, facing the first one can be added to create a pair of magnetic activable elements.

This second tip helps in focalizing the magnetic field lines and thus increases the magnetic field gradient in the microfluidic channel. As a consequence droplet splitting can be performed at lower magnetic particle content or at lower field intensity (i.e. lower current).

In another configuration, the second tip can be connected to an additional electromagnetic coil.

This can be done to increase the field intensity and thus to facilitate even more droplet splitting and particle extraction.

Figure 1:
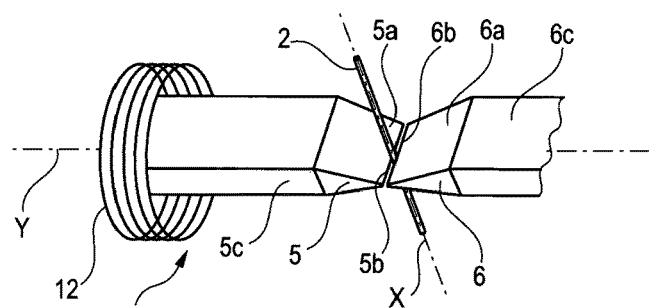
FIG. 1 is a partial diagrammatic view of a microfluidic device according to the invention.
Figure 2:
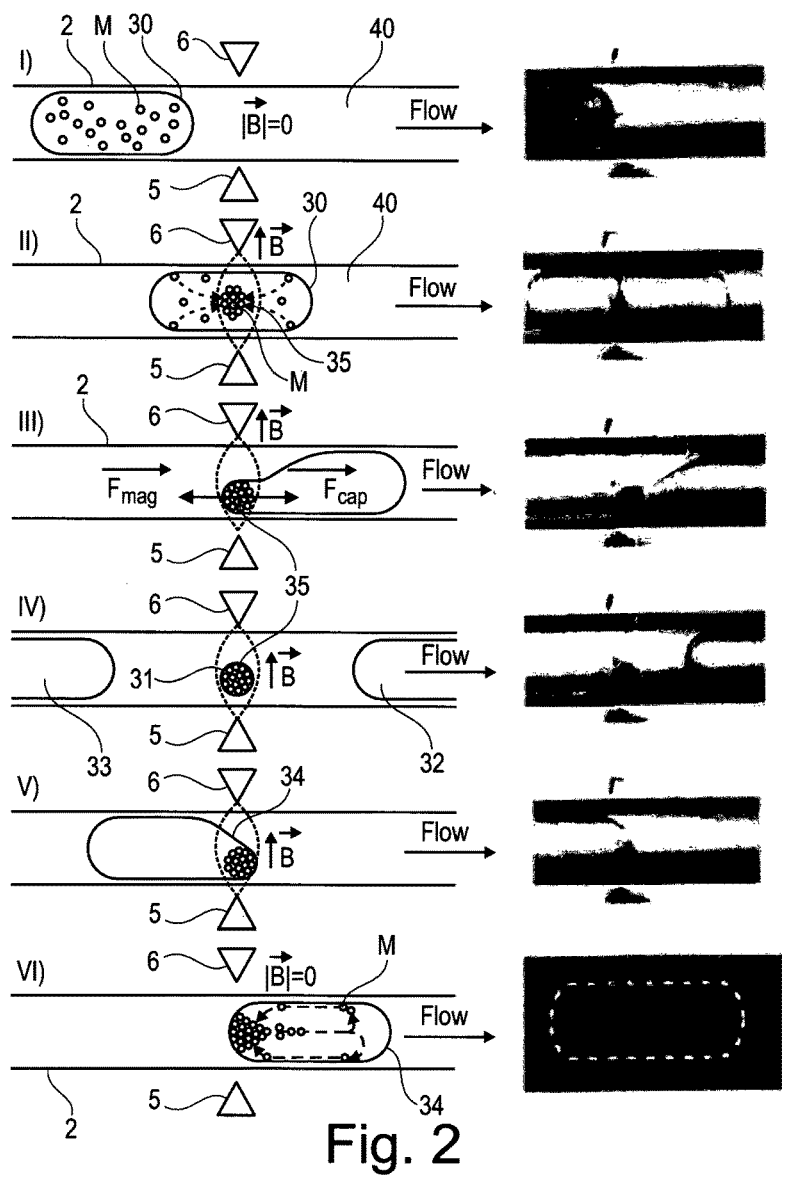

FIG. 1 shows a microfluidic system 1 comprising a micro channel 2 extending along a longitudinal axis X and a capture device 3 for generating a magnetic field to capture magnetic bodies and perform a method according to the invention, for example as illustrated on FIG. 2.

The device 3 comprises at least one activable magnetic element 5 and in the example shown comprises two activable magnetic elements 5 and 6. The pair of elements 5 and 6 is also referred to as "magnetic tweezers".

The magnetic elements 5 and 6 face each other and extend along an axis Y that is transverse to the axis X, preferably perpendicular to the axis X. Magnetic elements 5 and 6 each comprise a corresponding tip 5a and 6a having a cross-section perpendicular to axis Y that decreases toward the other tip. The cross-section of the tips 5a and 6a decreases when moving towards the microchannel 2 as shown.

In the example shown, each tip has an elongated cross-section and a respective edge 5b or 6b extending in a plane perpendicular to the axis X.

The two edges 5b and 6b may extend parallel to each other, as shown, being spaced by a distance that for example does not exceed five times the thickness of the micro channel in the direction Y.

The edges 5b and 6b may contact walls defining the micro channel, while being isolated by the walls from fluids circulating inside the micro channel.

The width of the tips 5a and 5b may exceed the width of the micro channel, as shown.

The tips 5a and 6a are preferably made out of a soft magnetic material such as µ metal so as to exhibit no or little remanent magnetism after excitation.

The tips 5a and 6a may be made integrally with a corresponding core 5c or 6c.

An excitation coil 12 is wounded around core 5c to generate an induction collinear with axis Y.

Figure 1A:
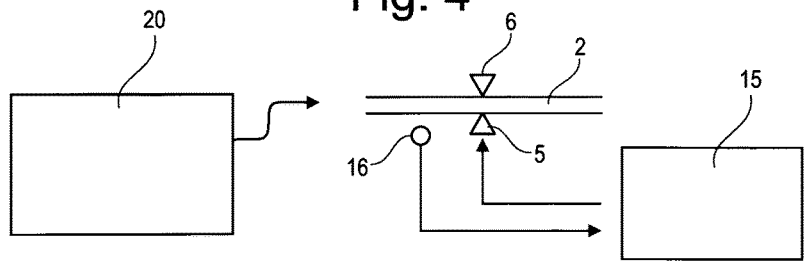
FIG. 1A is a diagrammatic view of a microfluidic device according to the invention, FIG. 2 diagrammatically represents the different steps of a bead-handling method according to the invention.

As shown in FIG. 1A, the coil 12 is connected to a controller 15 that may comprise a computer running a software configured to excite the coil 12 based on various input data and for example based on optical droplet detection.

A camera 16 may monitor the micro channel and provide the controller 15 with droplet detection information. This information enables automatic excitation of the coil 12 when a droplet is in the vicinity of the magnetic element 5 to perform for example the method illustrated in FIG. 2.

The system of the invention also comprises a microfluidic device 20 for generating droplets in the micro channel 2.

The device 20 comprises for example means forming droplets as disclosed by Chabert et al. in [2].

The device 20 may also be able to generate droplets via a Taylor cone phenomenon as disclosed in WO 2004/091763. Both publications are hereby incorporated by reference.

When exciting the coil 12, a magnetic field is generated by tip 5a and the magnetic field extends in the gap between tips 5a and 6a. The field is intense between the tips 5a and 6a and quite narrow which enables to capture magnetic beads within a droplet as shown in FIG. 2.

The captured magnetic beads are superparamagnetic particles.

The controller 15 is configured for periodic demagnetization of the activable magnetic elements 5 and 6 by powering the coil 12 with an alternative current of decreasing magnitude.

The activable magnetic element 5 is the only one in the example shown in FIG. 1 that is provided with a coil. In a variant non shown, the opposite element 6 is also provided with an excitation coil.

The coil 12 may be excited by a DC or AC current.

Preferably, as shown, the coil 12 is spaced from the edge of the tip, for example by at least 1 cm or 2 cm, which may reduce transfer of heat from the coil toward the micro channel.

The obtained experimental results are hereunder detailed.

EXAMPLES

Example 1: Particle Extraction

Experiments were performed with two kinds of devices. Device 1 was composed of a single magnetic tip made of soft magnetic alloys (AFK502R, Imphy Alloys Arcelor Mittal). An electromagnetic coil (33.5 mm diameter) made of 1000 loops of copper wire is used to control magnetization of one tip. The magnetic tip is placed perpendicularly with a Teflon tubing (300 µm ID and 600 µm OD, Sigma-Aldrich).

We used a home made cylindrical electromagnetic coil composed of around 1000 turns of insulated copper wire (0.8 mm diameter). The current intensity used ranges from 0 up to 4 A.

In a second type of device (device 2), a second tip, facing the first one can be added to create a magnetic tweezers configuration (reflection symmetry).

The different steps of the carried out method are shown in FIG. 2.

Droplets trains were produced in the Teflon tubing using an automated pipeting robot system.

Water droplets 30 were generated in fluorinated oil 40 (FC-40, 3M) with 3% of surfactant (1H,1H,2H,2H-perfluorodecan-1-ol, Fluorochem). Considering 100 nL droplets, we introduced 1 µg of particles M (1 µm, Dynal MyOne COOH Particles)

The system is composed of an aspirating tip (Teflon tubing Sigma) carried by a XYZ displacement stage and connected to a NeMesys syringe pump system (Cetoni), both controlled with Labview (National Instrument). Samples are stored in microtiter plate. In each well, aqueous samples are covered with fluorinated oil. The system sequentially aspirates aqueous solution and fluorinated oil in each well in order to produce a custom train of 80 nL droplets 30 with a spacing of 150 nL. During the droplets formation, the tube containing the magnetic particles suspension is mixed at least every 5 minutes in order to avoid beads sedimentation.

The typical velocity of the droplets trains was 1 mm/s. The oil flow rate was kept constant during all the experiment.

When passing through the magnetic tweezers 5 and 6, the current intensity in the electromagnet was switched from 0 up to 1.5 A for device 2 and from 0 to 2 A for device 1. The resulting magnetic field induces an attracting force toward the active tip. A magnetic bead cluster 35 is generated. While the droplet 30 is passing in between the tweezers, the cluster 35 is kept immobile until it reaches the water/oil interface of the droplet. When reaching the leading edge of the droplet, the magnetic pulling force acting on the bead-cluster is transferred to the water/oil interface and deforms the droplet. Above a certain threshold, the magnetic force overcomes capillary force and a particle-containing droplet 31 is split out of the mother droplet. The mother droplet 32 is dragged away by the oil flow while the extracted droplet 31, is retained in the trap. Obviously, this condition is fullfilled if the size of the resulting droplet, which is mainly dictated by the volume of the particle cluster, is smaller than the inner capillary size. In our experiments, the volumes of the extracted droplet was 1 nL.

The cluster-droplet 31 can be kept confined in the magnetic tweezers 5 and 6 until a new plug 33 comes into contact and merges spontaneously.

These different steps are diagrammatically shown in FIG. 2.

After merging, depending on the operation to be performed, the magnetic field can be:

a) maintained active to keep particles trapped in the trap while the droplet is passing.

b) released in order to re-suspend particles in a new droplet 34. In the latter case, the recirculating flows created by droplet motion give rise to internal hydrodynamic recirculation flows that enhances sample and particle mixing.

This strategy offers all the basic functions required for a bioassay namely particle washing, extraction and incubation in sub-microliter sample volumes. Confined droplets manipulation is advantageous as they offer small volumes, easy spatial and temporal handling and give rise to internal hydrodynamic recirculation flows that enhances sample mixing. As compared to earlier work, the use of a fluorinated-oil in fluorocarbon capillaries avoids contamination associated with contact between the water plug and the surface. Droplet containing magnetic particles can be manipulated individually, with very short response time, using electromagnetically actuated tweezers. This new approach allows a better extraction efficiency and lower sample volumes than reported e.g. in [3,4], and the easy and flexible implementation of complex protocols, when combined with a robotized drop formation platform [2] allowing the formation of "trains" comprising any number of droplets arbitrarily selected from a microtiter plate.

Several details concerning the method according to the invention are provided hereunder.

Capture Characterization

The magnetic force Fm used to extract a magnetic-particle cluster from the drop is related to the magnetic field gradient:

$$F_m = \left(\frac{Q}{\rho}\right)\chi\frac{B}{\mu_0}\nabla B$$

Here Q is the mass of magnetic particles, $\rho$ the mass density, $\chi$ the bead magnetic susceptibility, $\mu 0$ the permittivity of free space and B the magnetic flux density. The magnetic field gradient in the tubing may be influenced by the geometry of the tip and more particularly by its sharpness.

The adding of a second tip on the other side of the tubing may enable to concentrate the field lines. Consequently, a higher local value of the gradient field may be achieved in the tubing even if the second tip is not magnetized by a coil.

When magnet beads are attracted by tips, they produce a pressure on the droplet side resulting in a surface deformation. The bead extraction results from the balance between the magnetic and the capillary force. Fm has to be strong enough to overcome the capillary force created by the droplet surface deformation (FIG. 2) in order to break the surface. The capillary force Fc is related to the surface tension $\gamma$ between water and oil estimated at 10 mN·m−1 (Dorfman et al., 2005) [13] and the size of the bead cluster. The force is given by (Shikida et al., 2006).

$$F_C = 6^{\frac{1}{2}}\pi^{\frac{2}{3}}\gamma\left(\frac{Q}{\rho}\right)^{\frac{1}{2}}$$

Conditions Required for Bead-Cluster Extraction

Figures 3A, 3B:
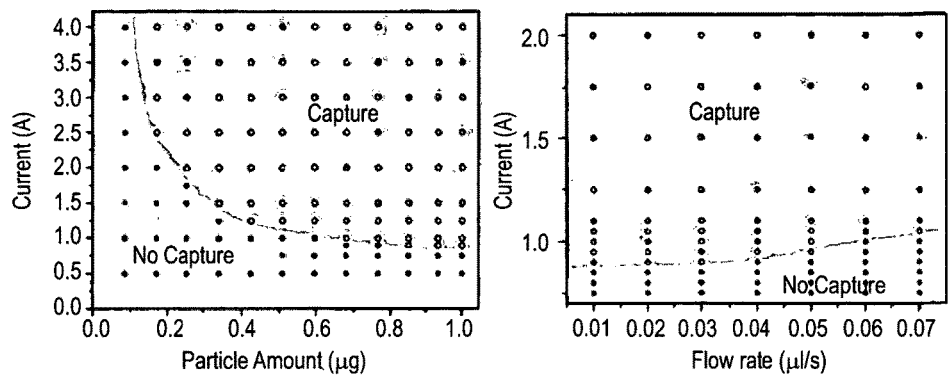
FIGS. 3A and 3B show phase diagrams illustrating the conditions required for bead-cluster extraction, FIG. 4 show an example of method according to the invention.

The relative influence of current intensity in the magnetic coil and particle load on bead-cluster extraction was investigated for a droplet velocity of about 300 μm/s which corresponds to a flow rate of 0.02 μL/s. The results are shown in FIG. 3A.

The relative influence of current intensity in the magnetic coil and droplet velocity on bead-cluster extraction was investigated for a particle loading of 0.8 μg/droplet. The results are shown in FIG. 3B.

We observed a small influence of the droplet speed on the ability to capture magnetic beads.

When the drop is moving too fast, the time to create the beads cluster close by the tips is reduced.

In some cases, the cluster formed does not contain the total amount of beads. This can have several consequences ranging from a decrease in the capture efficiency: some beads remain in the drop to the loss of extraction because the magnetic force necessary to extract beads is not able to overcome the capillary force. For high throughput application, the flow is directly related to the measurement capacity of the system. Then, the magnetic has to be tuned to be sure that all beads are extracted.

Merging and Mixing

Once the beads are extracted, the small droplet created is composed of magnetic particles and residual liquid. By measuring the droplet size and knowing the bead quantity in the cluster, the volume of the residual liquid is valued at 1 nL for initial 80 nL droplets containing 0.8 μg of beads.

As soon as the small cluster is in contact with another droplet, the merging always takes place.

Indeed the two droplets coalesce when the oil film between surfaces is thin enough and beads are suspended in without forming aggregates. Then magnetic particles are dispersed in the liquid leading to an 80-fold dilution factor for the residual liquid. Consequently, washing steps required for immunoassay can be performed only by merging and capturing successively beads in a buffer droplet which takes less than 1 s.

When particles are suspended from a cluster to a droplet in movement, they are compacted at the droplet end in a triangle-shaped area. However the bead mixing is efficient because plugs moving in tubing without wetting walls generate recirculating flow in oil and consequently in the drop too (Song et al., 2003) [14]. By this way, beads are dragged along those flow lines which lead to an active mixing in the entire droplet (FIG. 2).

Beads Capture Efficiency

We have discussed above the beads extraction driving forces and conditions. Here, we focus on the capture efficiency of our system. In order to quantify beads, fluorescent magnetic particles were prepared by saturating streptavidin coated beads with biotin atto 550. FIG. 8 shows the fluorescence profile of each plug after the capture and release processes.

Because of the compaction of magnetic beads at the end drop and because fluorescence observation is done on the back of the tubing, the intensity level reaches a constant maximum value in the middle of this area. As the MPs quantity is more related to the size of this area than the maximum fluorescence intensity, the fluorescence is integrated over the drop length. In this way, it becomes possible to discriminate the quantity of beads contained in each droplet. But the relation between the integrated fluorescence and MPs amount is not directly proportional that is why ratios between initial and final drops fluorescence are not conserved. As the MPs compaction leads to the underestimation of the real quantity of beads, the comparison of the fluorescence signal from initial drops and empty ones give us a capture efficiency higher than 99% which is actually an under the real value. The remaining magnetic particles seem to be trapped at the meniscus at the drop end. However this capture efficiency value is high enough to plan to use this system in a multi-step implementation such as sandwich immunoassay without losing biological materials.

Example 2: Immunoassay within Droplets

As previously described (example 1) the basic operation units required for an immunoassay can be performed using the droplet platform: beads confinement, beads washing, beads release and mixing in a given droplet as well as continuous fluorescence monitoring.

The immunoassay developed in this example is a sandwich immunoassay with capture antibody grafted on magnetic particles (from micro to nanoparticles). Secondary antibody (detection antibody) can be fluorescently labelled (FITC, Alexa . . . ) or conjugated with an enzyme (alkaline phosphatase, horse radish peroxydase . . . ). The immunoassay is based on the capture of the analyte of interest by the antibody capture grafted on the beads while the detection is performed using a secondary antibody targeting a different epitope. The analyte quantification is based on the amount of detectable secondary antibody. Using the magnetic droplet platform we developed, it is possible to incubate the beads with sample, to perform washing step, to incubate the beads with secondary antibody, to wash the beads and to perform the detection or to incubate the beads with an enzymatic substrate that will be transformed into a fluorescent product.

Experimental

Some more specific protocol details are now given.

The droplet immunoassay was developed to quantify thyroid stimulating hormone (TSH) in sub 100 nL serum sample as biomarker for the neonatal diagnosis of congenital hypothyroidism. The magnetic beads and all the immunoassay reagents are from Immunometrics TSH kit except MUP from Sigma. The capture antibody and detection antibody are monoclonal targeting different TSH epitopes.

Figure 4:
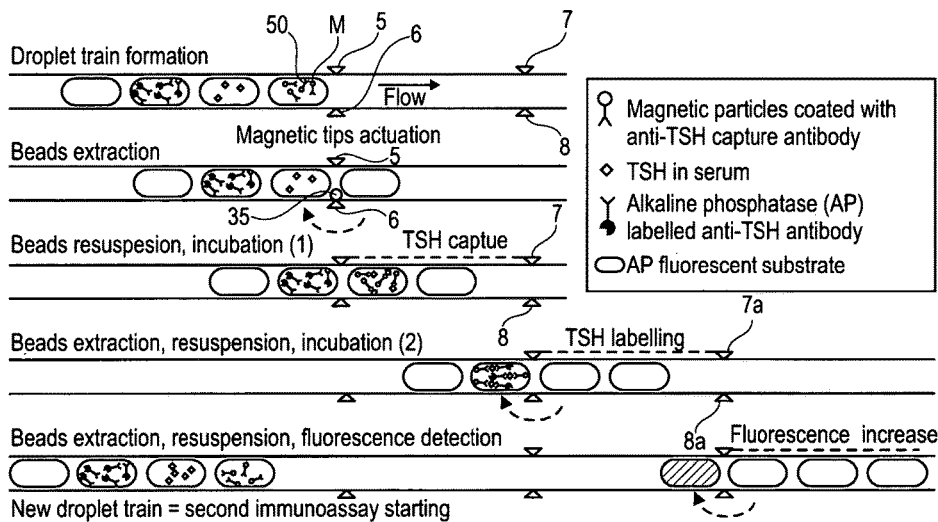

The droplet immunoassay is performed as following:
- An 8 droplets train (100 nl each droplet) is generated containing all the reagents required to perform the TSH quantitation as depicted FIG. 4. Low volume droplets were generated using a robotized injector [2] and transported by a perfluorinated oil inside perfluoroalkoxy capillaries (300 µm ID, Sigma). Droplet actuation was ensured by syringes pumps (Nemesys, Cetoni).
- First the magnetic beads M (carboxylic acid, 1.05 µm, MyOne Dynabeads, Invitrogen) are incubated with a horse serum spiked with various TSH concentrations ranging from 0 to 60 mIU/L.
- After an incubation time of 5 min, the immunological complex (capture antibody/TSH) 50 immobilized on the magnetic beads M is magnetically trapped by the magnetic tweezers 5 and 6.
- The beads are thus washed by flowing through the bead cluster 35 a TBS (tris buffered saline: 50 mM Tris.HCl, pH 7.4 and 150 mM NaCl) droplet to avoid the non-specific adsorption of proteins on the immunosupport.
- Using a second set of magnetic tweezers 7 and 8, the beads are magnetically confined and released in a droplet containing the secondary antibody coupled with the phosphatase alkaline enzyme (incubation time 5 min).
- Finally after a second washing step with 3 TBS droplets to remove unbound secondary antibody, a third set of magnetic tweezers 7a and 8a was used to release the particles in an enzymatic substrate (4-Methylumbelliferyl phosphate) droplet to perform the detection.

The magnetic particles were manipulated all along the droplets train by transferring them from a drop to the next one using a set of micro machined tips (AFK 502, Imphy Alloys) with an apex curvature radius <50 µm and magnetized on-demand with a home-made coil.

Principle of Detection

The principle of the detection consists in this example in using AP to transform a substrate into a product with properties detectably different. This could be, for instance, a change in colour, fluorescence, solubility, or redox properties.

For instance, in this example antibody labelled with PA are used with MUP as substrate. As an important remark, for use of PA, all buffers used should be devoid of phosphate, in order to avoid the phosphate competing with the substrate. We used TBS buffer as previously mentioned. The fluorescence signal is monitored using an epifluorescence microscope with a high sensitivity camera and dichroic equipment. The filter used is a "DAPI" one, with ($\lambda$exc=358 nm et $\lambda$em=461 nm). The observed fluorescence, which signs the production of 4-methylumbelliferone, is directly measured in the chip in real time from the epifluorescence objective.

Principle of Quantitation

There are two main different formats to monitor ELISA reaction end-point ELISA and kinetic ELISA. Kinetic ELISA differs from end-point ELISA as it is based on the enzyme substrate reaction kinetics. Indeed when the substrate is present in great excess, there is a linear relationship between the enzyme concentration and the velocity of substrate turnover. Both ELISA format can be performed using such platform.

Figure 6:
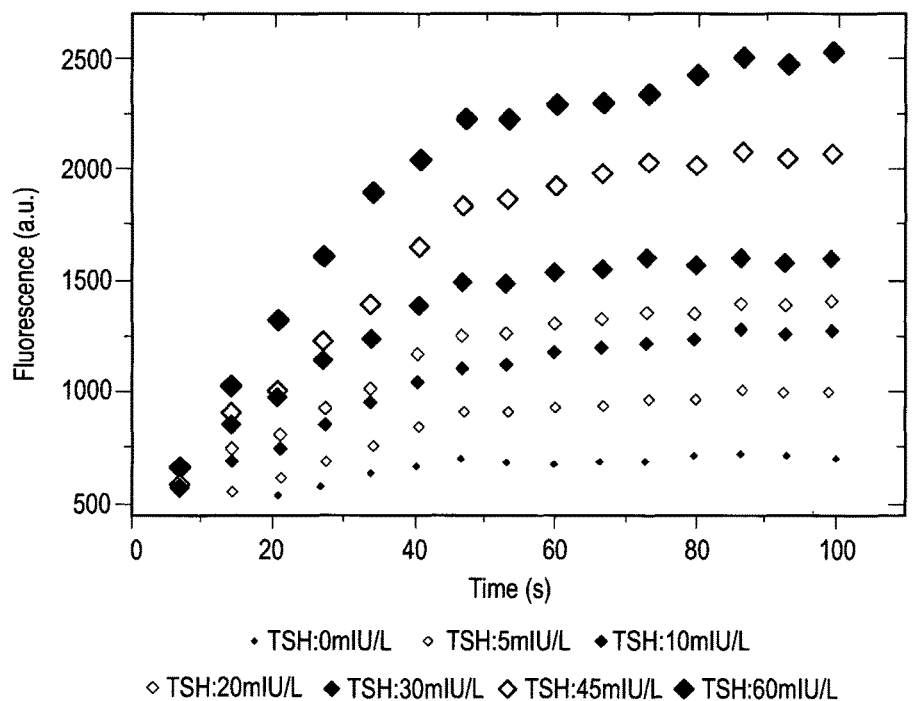

This example reports TSH quantitation within droplet by kinetic ELISA. FIG. 6 reports the temporal variation of the fluorescence signal within droplets with various initial TSH concentrations. As expected from enzymatic reaction, for a given period of time, the fluorescence signal increases linearly with time whereas at later time the concentration of fluorescent product reaches a plateau whereas the slope of reaction curves increases with the TSH concentration.

Figure 5:
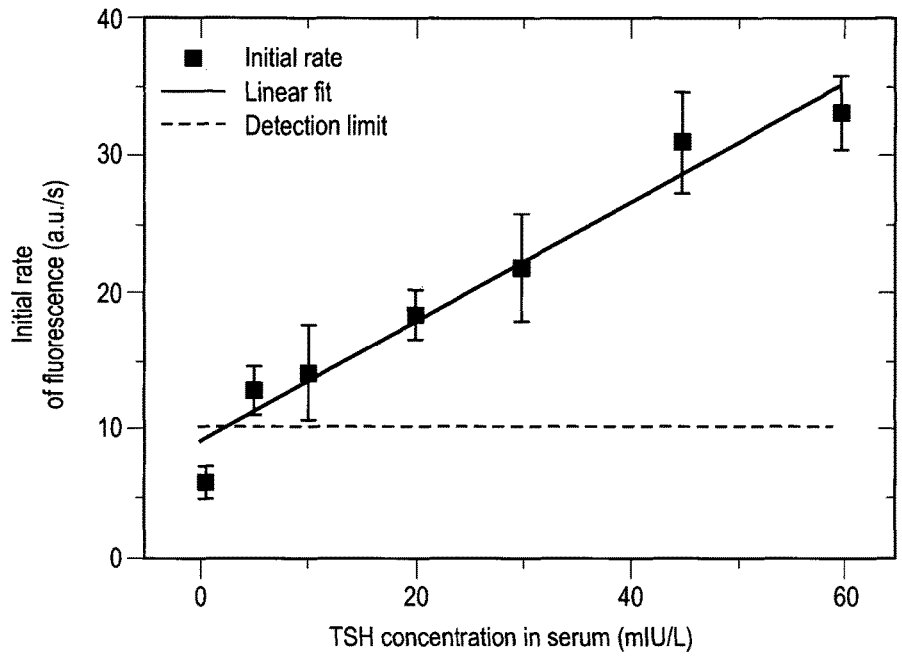

The immunoassay calibration curve was obtained by plotting the initial enzymatic rate against the TSH concentration (FIG. 5). The detection limit defined as three standard deviation of the background signal was 2 mIU/L equaling to 1.8 µM (Planells 1975) which is comparable with conventional colorimetric kinetic ELISA (2.3 mIU/L). The complete immunoassay is performed in less than 10 minutes compared to the 2 h30 required for the conventional ELISA.

As soon as the first step is performed on the drop train, it is possible to start a second analysis since tweezers are controlled independently. By this way, the immunoassay output is controlled by the droplet train length. This leads to an analysis throughput of 120 analyses per hour on sub 100 nL samples.

Results and Discussion

This strategy was applied to an immunoassay dedicated to neonatal diagnosis of congenital hypothyroidism (CH), a disease of high prevalence (1:2000 to 1:4000 newborns). The prognosis of infants treated early is excellent whereas untreated CH leads to severe development problems.

The clinical diagnosis of CH is mainly based on an elevated concentration of thyroid stimulating hormone (TSH>30 mIU/L serum). Using this microfluidic platform, the whole immunoassay is performed in 10 min in sub-100 nL volume sample (as compared to 2 h30 and 200 µL for conventional ELISA) which are essential criteria for neonatal diagnosis. The analytical sequence of the sandwich ELISA we developed is presented in FIG. 4. The quantitation was performed by monitoring continuously the increase of fluorescence as a function of substrate incubation time.

The TSH concentration is thus determined by the slope of the reaction curve corresponding to the enzymatic initial rate (FIG. 6). The detection limit defined as three standard deviation of the background signal was 2 mIU/L equaling to 1.8 µM (FIG. 5) which is comparable with conventional colorimetric ELISA, and meets the standard of congenital hypothyroidism diagnosis.

FIG. 7 show that results in microfluidic droplets fulfill the standard sensitivity required for TSH detection (standard threshold 30 mIU/L in serum). Results (normalized) compared to conventional colorimetric batch analysis. Error bars refers to triplicate measurements.

More generally, a sensitivity in the picomolar range paves the way for numerous analysis of disease biomarkers present in this concentration range in biological matrix. Current investigations on multiplexing show that, once started, the platform allows for continuous droplet-train generation and analysis associated to a maximum analysis rate above 120 analysis/hour and appears as very appealing for the development of a high throughput strategy.

Conclusion

We successfully developed a flexible immunoassay platform based on confined droplet and magnetic particle handling. The present work was applied to congenital hypothyroidism diagnosis but can be extended to almost any immunoassay. Our results show similar sensitivity performances compared to batch protocol while providing a 1000-fold volume reduction and a total analysis time shortening from 2 h30 to 10 min. This approach paves the way for automated and high throughput screening of biomarker on low volume sample.

Example 3: Magnetic Bead-Based Immuno-Agglutination Assay in Confined Droplets

As shown in FIG. 9, an aggregation step is performed in water in oil droplets 30 and is induced by magnetic confinement to enhance magnetic beads (MBs) M collision frequencies thus favoring aggregates formation [17].

Confined droplets 30 in fluorinated oil [18,19] allow individual compartmentalization preventing cross contaminations. Moreover, the possibility to generate them in large number in a "pipeline" format gives access to reliable and high throughput analyses in simple chip designs.

First demonstration of the assay was performed (FIG. 9) using streptavidin coated MBs (1 µm) M (surface-functionalized magnetic particles) and biotinylated phosphatase alkaline (b-PA) (target: 38) as a model. As detailed hereunder, the magnetic particles M provides a plurality of binding sites 39a.

Droplets 30 were generated in a Teflon tube by sequentially aspirating defined volumes of oil and sample (containing the MBs M and the target 38, respectively) from a microtiter plate. (1) Droplets 30 were generated from a mixture of MBs M that was first incubated with b-PA 38 for 5 minutes and further transported in a Teflon tubing. The target 38 can thus be captured on the binding sites 39a of the particles M. The droplets containing free MBs were further transported towards magnetic tweezers (2) 5 and 6. When passing in between the magnetic tweezers 5 and 6, the MBs were magnetically confined to enhance aggregates 35 formation.

Once passing the tweezers 5 and 6, the internal recirculation flows in the droplet induce shear forces that favors MBs re-dispersion. This process prevents non-specific aggregation but preserves specific interactions between particles, which stay in the aggregated state and still forms an aggregate 35a (FIGS. 9, 10A and B). As it can be seen from FIG. 9, the aggregated magnetic particles are linked to each other by a bridge 39 having the following structure: binding site 39a of a first magnetic particle-target 38-binding site 39b of a second magnetic particle different from the first.

FIG. 10 shows bright field micrographs of MBs agglutination in droplets at 0 (A) and 100 ng/mL (B) of target. Changes in integrated transmitted light for the blank ($S_{blank}$) and assay ($S_{assay}$) experiments are monitored in transmission using simple visible low-cost USB camera 60. The signal is defined as $(1-S_{assay}/S_{blank})$. C) Calibration curves for b-PA target after 5 min incubation were obtained for three different concentrations of MBs: 1 (red), 2 (blue), 3 mg/mL (green). The insert is a focus on the 0-80 ng/mL target concentration range.

The assembly comprises a light source 61 configured to irradiate the droplet, the optical detector 60 being configured to measure the quantity of light from the light source absorbed by the droplet.

The light source 61 and the camera 60 allows to visualize the content of the detection zone 70 of the microchannel.

The detection consists in measuring the change in the integrated light absorption across the droplet, induced by the aggregation process. Beads in the aggregated state occupy less area in the droplet perpendicular to the observation direction, and thus aggregation increases the transmission signal.

When present in the detection zone 70, at least 10%, preferably 50%, preferably 70%, more preferably 80%, of the magnetic particles contained in the droplet may be in an aggregated form.

FIG. 11 highlights that the application of B increases drastically the aggregation kinetics. Using a 1 mg/mL MBs concentration, the limit of detection was about 100 µM (FIG. 10C) which meets the requirements of most immunodiagnostics.

This droplet based platform provides analysis at high throughput (300 analyses per hour) and low cost. The set-up is composed of simple items while droplets format reduces the sample volumes down to 80 nL. Moreover, the integration of magnetic tweezers allows extraction and transfer of MBs from drop to drop thus allowing full automation of the assay steps.

In a variant, the activable magnetic elements 5 or 6 may have the geometry depicted in FIGS. 12 to 14, and 15 to 15F.

As shown in FIGS. 12 and 13, the activable magnetic element 5 comprises a tip 5a whose width w and thickness t decreases along the longitudinal axis Y of the tip 5. The activable magnetic element 5 shown has a convex shape.

Figure 15:
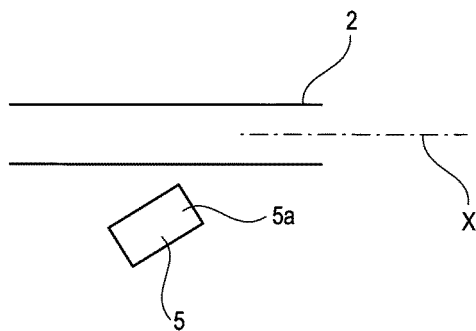
Figure 15A:
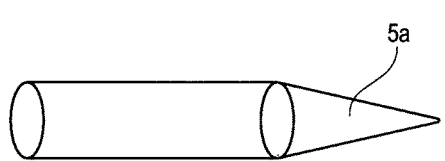
Figure 15B:
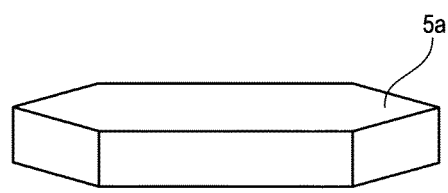
Figure 15C:
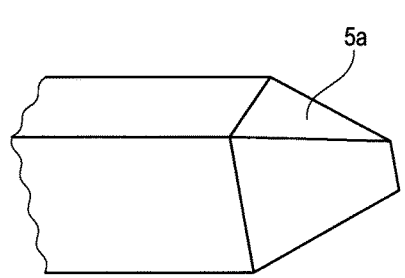
Figure 15D:
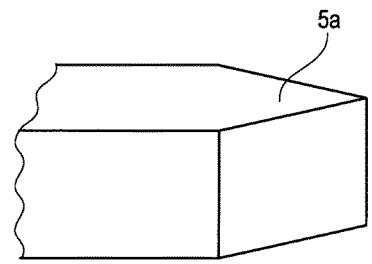
Figure 15E:
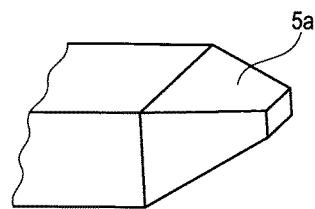
Figure 15F:
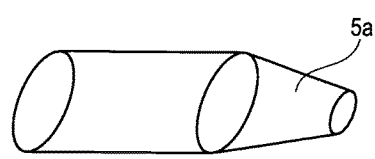

As shown in FIG. 15, the magnetic element 5 may have a parallelepiped shape with a tip having a decreasing section when moving towards the micro channel. The tip 5a extends as shown transversely, in particular perpendicularly, to the longitudinal X of the microchannel.

In a variant, the magnetic element has a cubic shape.

Figure 16A:
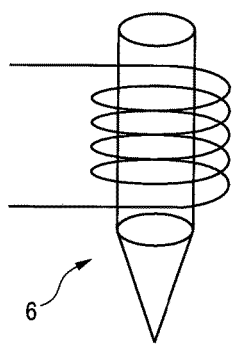
FIGS. 16A and 16B show examples of activable magnetic element, and FIG. 17 show an embodiment of a micro channel according to the invention.

FIG. 16A further shows an embodiment of a directly activable magnetic element which is the core of an electromagnet.

Figure 16B:
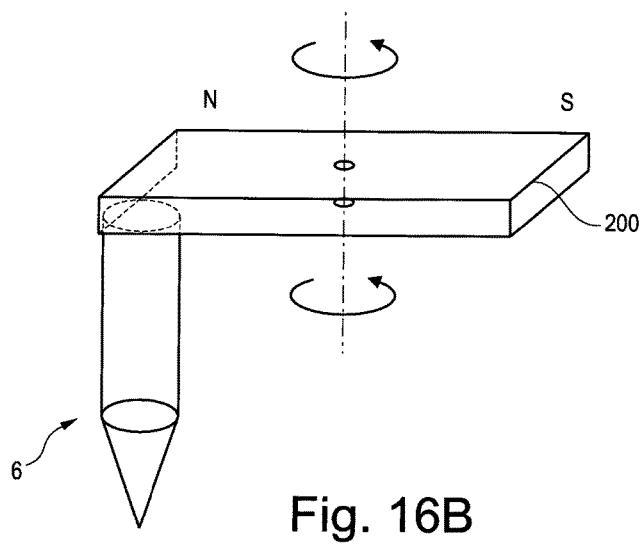

FIG. 16B shows an example of a soft magnetic element used as an activable magnetic element, wherein a permanent magnet can be brought in close proximity of said soft magnetic element by mechanical means.

The permanent magnet can be rotated in order to have its pole in contact with one side of the core, in such case, the core is activated, or rotated in order to be no more in contact with such core, in such case the core is inactivated.

Figure 17:
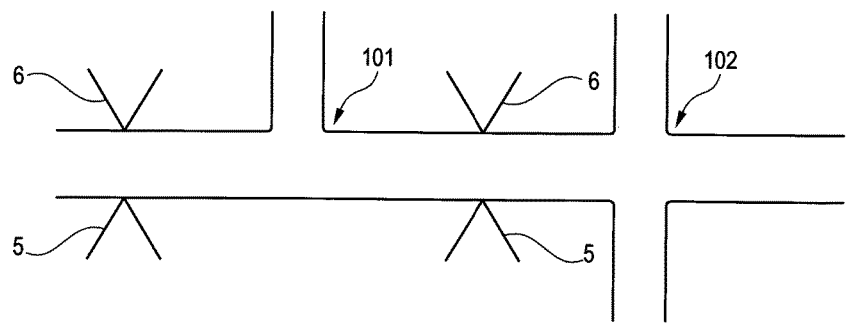

FIG. 17, further shows an embodiment of a micro channel which comprises branching such as side branching 101, or cross-branchings 102. The branching areas are located along the micro channel in areas distant from the areas facing the activable magnetic elements 5 and 6 as shown.

REFERENCES

[1] R. S. Sista, A. E. Eckardt, V. Srinivasan, M. G. Pollack, S. Palanki and V. K. Pamula, *Heterogeneous immunoassays using magnetic beads on a digital microfluidic platform*, Lab on a Chip, vol. 8(12), pp. 2188-96, (2008).
[2] M. Chabert, K. D. Dorfman, P. de Cremoux, J. Roeraade and J-L. Viovy, *Automated microdroplet platform for sample manipulation and polymerase chain reaction*, Analytical Chemistry, vol. 78(22), pp. 7722, (2006).
[3] H. Tsuchiya, M. Okochi, N. Nagao, M. Shikida and H. Honda, *On-chip polymerase chain reaction microdevice employing a magnetic droplet-manipulation*, Sensors and Actuators B, vol. 130(2), pp. 583-588, (2008).
[4] D. Lombardi and P. S. Dittrich, *Droplet microfluidics with magnetic beads: a new tool to investigate drug-protein interactions*, Analytical and bioanalytical chemistry, vol. 399(1), pp. 347, (2010).
[5] Clague, A., & Thomas, A. (2002). Neonatal biochemical screening for disease. *Clinica Chimica Acta*, 315(1-2), 99-110.
[6] Shikida, Mitsuhiro, Takayanagi, Kentaro, Honda, Hiroyuki, Ito, H., & Sato, Kazuo. (2006a). Development of an enzymatic reaction device using magnetic bead-cluster handling. *Journal of Micromechanics and Microengineering*, 16(9), 1875-1883. doi: 10.1088/0960-1317/16/9/017.
[7] Shikida, Mitsuhiro, Takayanagi, Kentaro, Honda, Hiroyuki, Ito, H., & Sato, Kazuo. (2006b). Development of an enzymatic reaction device using magnetic bead-cluster handling. *Journal of Micromechanics and Microengineering*, 16(9), 1875-1883. doi: 10.1088/0960-1317/16/9/017.
[8] Zhang, Y., Park, S., Liu, K., Tsuan, J., Yang, S., & Wang, T.-H. (2010). A surface topography assisted droplet manipulation platform for biomarker detection and pathogen identification. Lab on a chip, (207890). doi: 10.1039/c01c00296h.
[9] Long, Z., Shetty, A. M., Solomon, M. J., & Larson, R. G. (2009). Fundamentals of magnetactuated droplet manipulation on an open hydrophobic surface. *Lab on a chip*, 9(11), 1567-75. doi: 10.1039/b819818g.
[10] Lehmann, U., Hadjidj, S., Parashar, V., Vandevyver, C., Rida, a, & Gijs, M. (2006). Two dimensional magnetic manipulation of microdroplets on a chip as a platform for bioanalytical applications. *Sensors and Actuators B: Chemical*, 117(2), 457-463. doi: 10.1016/j.snb.2005.12.053.
[11] Lafranchi, S. H. (2010). Newborn screening strategies for congenital hypothyroidism: an update. *Journal of Inherited Metabolic Disease*, 33, 225-233. doi: 10.1007/s10545-010-9062-1.
[12] Al Hetlani et al., MicoTAS 2010 proceedings, CBMS publ, pp 1817-1819.
[13] Dorfman, K. D., Chabert, M., Codarbox, J.-H., Rousseau, G., Cremoux, P. de, & Viovy, J.-L. (2005). Contamination-free continuous flow microfluidic polymerase chain reaction for quantitative and clinical applications. *Analytical chemistry*, 77(11), 3700-4. doi: 10.1021/ac050031i.
[14] Song, H., Tice, J. D., & Ismagilov, R. F. (2003). A microfluidic system for controlling reaction networks in time. *Angewandte Chemie*, 42(7), 767-772.
[15] "A One-step homogeneous immunoassay for cancer biomarker detection using gold nanoparticle probes coupled with dynamic light scattering," X. Liu, Q. Dai, L. Austin, J. Coutts, G. Knowles, J. Zou, H. Chen and Q. Huo, Journal of the American Chemical Society, 130, 2780 (2008).
[16] "Three-Dimensional Magnetic Focusing of Superparamagnetic Beads for On-Chip Agglutination Assays" R. Afshar, Y. Moser, T. Lehnert and M. A. M. Gijs, Analytical Chemistry, 83, 1022 (2011).
[17] "Acceleration of the recognition rate between grafted ligands and receptors with magnetic forces," J. Baudry, C. Rouzeau, C. Goubault, C. Robic, L. Cohen-Tannoudji, A. Koenig, E. Bertrand and J. Bibette, Proceedings of the National Academy of Sciences of the United States of America, 103, 16076 (2006).
[18] "Reactions in Droplets in Microfluidic Channels," H. Song, D. L. Chen and R. F. Ismagilov, Angewandte Chemie International Edition, 45, 7336 (2006).
[19] "ABO, D Blood Typing and Subtyping Using Plug-Based Microfluidics," T. R. Kline, M. K. Runyon, M. Pothiawala, and R. F. Ismagilov, Analytical Chemistry, 80, 6190 (2008).

The expression "comprising/containing" must be understood, unless otherwise specified, as "comprising at least one/containing at least one".

The expression "forming a" must be understood, unless otherwise specified, as "forming at least one".

The expression "comprised between . . . and . . . " must be understood, unless otherwise specified, as including the bounds.

The invention claimed is:
1. A microfluidic system comprising:
    a microfluidic device comprising a microchannel, in the microchannel, a sequence of droplets of at least one first fluid in a surrounding immiscible second fluid, at least one droplet containing magnetic particles being transported by a flow of said second fluid through a portion of the microchannel;
    a device for generating inside the portion of the microchannel a magnetic field, said device comprising an activable magnetic element,
    activation of the activable magnetic element creating the magnetic field in the portion of the microchannel causing the magnetic particles to be captured in said portion,
    wherein the activable magnetic element comprises:
        a core that is reversibly magnetizable, and
        a tip made out of a soft magnetic material and having an acute tip angle in one direction only, the tip being magnetically coupled to the core, the tip having a cross-sectional area decreasing towards the microchannel, the decreasing cross-sectional area creating a convergence of magnetic field lines inside said tip, wherein the end of the tip proximal the microchannel has a longitudinal dimension greater than a width of the microchannel.
2. The system according to claim 1, wherein the core is surrounded by a conducting coil connected to a current generator.
3. The system according to claim 1, further comprising a plurality of activable magnetic elements.
4. The system according to claim 1, wherein the magnetic particles do not comprise ferromagnetic particles.
5. The system according to claim 1, wherein the magnetic particles are surface-functionalized.
6. The system according to claim 1, wherein the magnetic particles form an aggregate of magnetic particles.

7. The system according to claim 1, the microchannel containing a plurality of droplets containing magnetic particles.

8. The system according to claim 1, wherein the device for generating the magnetic field inside the microchannel creates inside the microchannel a magnetic field having field lines which are not collinear to the longitudinal axis of the microchannel so as to capture the magnetic particles.

9. The system according to claim 1, further comprising an acoustic wave generator for exposing the inside of the microchannel to ultrasonic waves.

10. The system according to claim 1, wherein the microfluidic system further comprises a syringe pump.

11. The system according to claim 1, wherein the device comprises additional activable magnetic elements which face the activable magnetic element across the microchannel.

12. The system according to claim 1, wherein the end of the tip of the activable magnetic element proximal the microchannel is a flat end.

13. The system according to claim 12, wherein the flat end of the tip occupies an area that is smaller than the rest of the tip.

14. The system according to claim 13, wherein the area of the flat end of the tip occupies less than 2% of the area of the rest of the tip.

15. The system according to claim 1, wherein the acute tip angle of the activable magnetic element is smaller than 45°.

16. The system according to claim 1, wherein the end of the tip proximal the microchannel has a dimension measured along a longitudinal axis of the microchannel that is less than a length of one of the droplets in the sequence of droplets.

17. The system according to claim 16, wherein the ratio of the dimension of the end of the tip to the length of the droplet is less than 1:5.

18. The system according to claim 1, wherein the microchannel passes several times in the vicinity of the convergence of magnetic field lines.

19. The system according to claim 1, wherein the activable magnetic element is one of a pair of activable magnetic elements which face each other across the microchannel.

20. An assembly comprising:
the microfluidic system according to claim 1, and
a detector for measuring at least one characteristic of a droplet containing magnetic particles present in the microchannel.

21. A method of manipulating magnetic particles, the method using the microfluidic system according to claim 1 and comprising:

capturing and aggregating the magnetic particles contained in a droplet in the vicinity of at least one activable magnetic element by submitting the magnetic particles to a magnetic field generated by the at least one activable magnetic element, wherein the at least one activable magnetic element creates conditions chosen from a magnetic field intensity being comprised between 10 mT and 1 T and a magnetic field gradient being comprised between 10 and 10000 T/m along the longitudinal axis of the microchannel, the magnetic particles being surface functionalized, each of the surface functionalized magnetic particles providing at least one binding site for a target, the target being present in the droplet containing the magnetic particles.

22. A method of extracting at least one magnetic particle from a first primary droplet of a first fluid flowing in a microchannel, said method using the microfluidic system according to claim 1 and comprising:

capturing the at least one magnetic particle in the vicinity of at least one activable magnetic element by submitting the at least one magnetic particle to a magnetic field generated by the at least one activable magnetic element, deforming the first primary droplet, and splitting the first primary droplet into a first secondary droplet and a second secondary droplet, the first secondary droplet comprising the at least one magnetic particle and remaining captured by the magnetic field in the vicinity of the at least one activable magnetic element to extract the at least one particle from the first primary droplet.

23. A method of manipulating at least one magnetic particle comprising:

extracting the at least one magnetic particle from a first primary droplet of a first fluid flowing in a microchannel according to the method defined in claim 22, and releasing the at least one magnetic particle by modifying an intensity and/or gradient of the magnetic field created by the at least one activable magnetic element.

* * * * *